(12) United States Patent
Ramstack et al.

(10) Patent No.: US 7,371,406 B2
(45) Date of Patent: May 13, 2008

(54) PREPARATION OF INJECTABLE SUSPENSIONS HAVING IMPROVED INJECTABILITY

(75) Inventors: J. Michael Ramstack, Lunenburg, MA (US); M. Gary I. Riley, Cambridge, MA (US); Stephen E. Zale, Hopkinton, MA (US); Joyce M. Hotz, Cincinnati, OH (US); Olufunmi L. Johnson, Cambridge, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 134 days.

(21) Appl. No.: 10/681,142

(22) Filed: Oct. 9, 2003

(65) Prior Publication Data

US 2004/0208938 A1 Oct. 21, 2004

Related U.S. Application Data

(60) Division of application No. 10/259,949, filed on Sep. 30, 2002, now Pat. No. 6,667,061, which is a continuation of application No. 09/577,875, filed on May 25, 2000, now Pat. No. 6,495,164.

(51) Int. Cl.
*A61K 9/14* (2006.01)
*A61F 13/00* (2006.01)
*A61F 2/00* (2006.01)

(52) U.S. Cl. .................. 424/489; 424/422; 424/423
(58) Field of Classification Search .................. 424/489
See application file for complete search history.

(56) References Cited

U.S. PATENT DOCUMENTS

| | | | |
|---|---|---|---|
| 3,523,906 A | 8/1970 | Vrancken et al. | |
| 3,691,090 A | 9/1972 | Kitajima et al. | |
| 3,700,215 A | 10/1972 | Hardman et al. | |
| 3,737,337 A | 6/1973 | Schnoring et al. | |
| 3,773,919 A | 11/1973 | Boswell et al. | |
| 3,891,570 A | 6/1975 | Fukushima et al. | |
| 3,960,757 A | 6/1976 | Morishita et al. | |
| 4,221,862 A | 9/1980 | Naito et al. | |
| 4,384,975 A | 5/1983 | Fong | |
| 4,389,330 A | 6/1983 | Tice et al. | |
| 4,530,840 A | 7/1985 | Tice et al. | |
| 4,803,075 A * | 2/1989 | Wallace et al. .............. | 424/423 |
| 4,818,517 A | 4/1989 | Kwee et al. | |
| 4,940,588 A | 7/1990 | Sparks et al. | |
| 5,066,436 A | 11/1991 | Komen et al. | |
| 5,385,738 A | 1/1995 | Yamahira et al. | |
| 5,407,609 A | 4/1995 | Tice et al. | |
| 5,428,024 A | 6/1995 | Chu et al. | |
| 5,478,564 A | 12/1995 | Wantier et al. | |
| 5,486,362 A * | 1/1996 | Kitchell et al. ............. | 424/426 |
| 5,540,912 A | 7/1996 | Roorda et al. | |
| 5,541,172 A | 7/1996 | Labric et al. | |
| 5,612,346 A | 3/1997 | Mesens et al. | |
| 5,627,158 A * | 5/1997 | Cho-Chung .................. | 514/44 |
| 5,631,021 A * | 5/1997 | Okada et al. ............... | 424/451 |
| 5,650,173 A | 7/1997 | Ramstack et al. | |
| 5,654,008 A * | 8/1997 | Herbert et al. .............. | 424/489 |
| 5,654,010 A | 8/1997 | Johnson et al. | |
| 5,656,297 A | 8/1997 | Bernstein et al. | |
| 5,656,299 A | 8/1997 | Kino et al. | |
| 5,658,593 A | 8/1997 | Orly et al. | |
| 5,667,808 A | 9/1997 | Johnson et al. | |
| 5,688,801 A | 11/1997 | Mesens et al. | |
| 5,747,058 A | 5/1998 | Tipton et al. | |
| 5,770,231 A | 6/1998 | Mesens et al. | |
| 5,792,477 A | 8/1998 | Rickey et al. | |
| 5,858,410 A * | 1/1999 | Muller et al. ............... | 424/489 |
| 5,871,778 A | 2/1999 | Kino et al. | |
| 5,916,598 A | 6/1999 | Rickey et al. | |
| 5,922,025 A * | 7/1999 | Hubbard ...................... | 424/423 |
| 5,942,253 A | 8/1999 | Gombotz et al. | |
| 5,965,168 A | 10/1999 | Mesens et al. | |
| 6,034,175 A * | 3/2000 | Hutchinson ................ | 525/54.1 |
| 6,077,843 A | 6/2000 | Fran.cedilla.ois et al. | |

(Continued)

FOREIGN PATENT DOCUMENTS

EP 0 486 959 A1 5/1992

(Continued)

OTHER PUBLICATIONS

Akers, M.J. et al., "Formulation Design and Development of Parenteral Suspensions," Journal of Parenteral Science and Technology, 41(3):88-95 (May-Jun. 1987).

(Continued)

*Primary Examiner*—S. Tran
(74) *Attorney, Agent, or Firm*—Andrea G. Reister; Covington & Burling LLP

(57) ABSTRACT

Injectable compositions having improved injectability. The injectable compositions include microparticles suspended in an aqueous injection vehicle having a viscosity of at least 20 cp at 20° C. The increased viscosity of the injection vehicle that constitutes the fluid phase of the suspension significantly reduces in vivo injectability failures. The injectable compositions can be made by mixing dry microparticles with an aqueous injection vehicle to form a suspension, and then mixing the suspension with a viscosity enhancing agent to increase the viscosity of the fluid phase of the suspension to the desired level for improved injectability.

20 Claims, No Drawings

U.S. PATENT DOCUMENTS

| | | | |
|---|---|---|---|
| 6,306,425 B1 * | 10/2001 | Tice et al. | 424/426 |
| 6,495,155 B1 | 12/2002 | Tice et al. | |
| 6,495,164 B1 | 12/2002 | Ramstack et al. | |
| 6,500,448 B1 | 12/2002 | Johnson et al. | |
| 6,555,544 B2 * | 4/2003 | Francois et al. | 514/259.41 |

FOREIGN PATENT DOCUMENTS

| | | |
|---|---|---|
| EP | 0831773 | 12/1999 |
| WO | WO 89/03678 | 5/1989 |
| WO | WO 90/13361 | 11/1990 |
| WO | WO 94/10982 | 5/1994 |
| WO | WO 94/25460 A1 | 11/1994 |
| WO | WO 95/13799 | 5/1995 |
| WO | WO 9513799 A1 * | 5/1995 |
| WO | WO 96/01652 A1 | 1/1996 |
| WO | WO 96/40049 | 12/1996 |
| WO | WO 97/14408 A1 | 4/1997 |
| WO | WO 97/41837 | 11/1997 |
| WO | WO 97/44039 A1 | 11/1997 |
| WO | WO 9744039 A1 * | 11/1997 |
| WO | WO 99/12549 | 3/1999 |
| WO | WO 99/25354 A2 | 5/1999 |
| WO | WO 0024374 A1 * | 5/2000 |

OTHER PUBLICATIONS

Beck, L.R. et al., Biology of Reproduction, 28:186-195 (Feb. 1983).
Bodmeier, R. et al., International Journal of Pharmaceuticals, 43:179-186 (1988).
Cajavec, Stanislav et al., "The primary chicken vaccination against Newcastle disease with antigenic virus subunits prepared in a water-in-oil-in-water emulsion," Periodicum Biologorum, 99(1):39-44 (1997).
Cha, Y and Pitt, C.G., "The Acceleration of Degradation-Controlled Drug Delivery from Polyester Microspheres," Journal of Controlled Release, 8:259-265 (1989).
Cha, Y. and Pitt, C.G., "A One-Week Subdermal Delivery System for L-Methadone Based on Biodegradable Microparticles," Journal of Controlled Release, 7:69-78 (1988).
"How to Avoid Clogging of Insulin Syringes," Diabetes Forcase, pp. 27-29 (Nov.-Dec. 1976).
Jalil, R. et al., Journal of Microencapsualtion, 7(3):297-319 (Jul.-Sep. 1990).
Li, Wen-I et al., Journal of Controlled Release, 37:199-214 (Dec. 1995).
Maulding, H.V. et al., "Biodegradable Microparticles: Acceleration of Polymeric Excipient Hydrolytic Rate by Incorporation of a Basic Medicament," Journal of Controlled Release, 3:103-117 (Mar. 1986).
Pharmaceutical Dosage Forms Disperse Systems, edited by Herbert A. Lieberman, Martin M. Rieger, Gilbert I. Bank, second edition, Chapter 7, "Injectable Emulsions and Suspensions," 1:261-318.
Pharmaceutical Dosage forms Disperse Systems, edited by Herbert A. Lieberman, Martin M. Rieger, Gilbert I. Bank, second edition, Chapter 7, "Viscosity-Imparing Agents in Disperse Systems," 2:287-313 (1996).
Sah, Hongkee et al., Pharmaceutical Research, 13:360:367 (Mar. 1996).
Sato, Toyomi et al., Pharmaceutical Research, 5:21-30 (1988).
Zingerman, J.R. et al., "Automatic injector apparatus for studying injectability of parenteral formulations for animal health," International Journal of Pharmaceuticals, 36: 141-145 (1987).
Beck et al (1983) *Biology of Reproduction* 28, 186-195.
Maulding et al (1986) *Journal of Controlled Release* 3, 103-117.

* cited by examiner

PREPARATION OF INJECTABLE SUSPENSIONS HAVING IMPROVED INJECTABILITY

BACKGROUND OF THE INVENTION

1. Field of the Invention

The present invention relates to preparation of injectable compositions. More particularly, the present invention relates to injectable suspensions having improved injectability, and to methods for the preparation of such injectable suspensions.

2. Related Art

Injectable suspensions are heterogeneous systems that typically consist of a solid phase dispersed in a liquid phase, the liquid phase being aqueous or nonaqueous. To be effective and pharmaceutically acceptable, injectable suspensions should preferably be: sterile; stable; resuspendable; syringeable; injectable; isotonic; and nonirritating. The foregoing characteristics result in manufacturing, storage, and usage requirements that make injectable suspensions one of the most difficult dosage forms to develop.

Injectable suspensions are parenteral compositions in that they are introduced into an organism or host by means other than through the gastrointestinal tract. Particularly, injectable suspensions are introduced into a host by subcutaneous (SC) or intramuscular (IM) injection. Injectable suspensions may be formulated as a ready-to-use injection or require a reconstitution step prior to use. Injectable suspensions typically contain between 0.5% and 5.0% solids, with a particle size of less than 5 µm for IM or SC administration. Parenteral suspensions are frequently administered through needles about one-half to two inches long, 19 to 22 gauge, with an internal diameter in the range of 700 to 400 microns, respectively.

To develop an effective and pharmaceutically acceptable injectable suspension, a number of characteristics must be evaluated. These characteristics include syringeability, injectability, clogging, resuspendability, and viscosity. As will be readily apparent to one skilled in the art, other characteristics and factors should be considered in developing an injectable suspension (see, for example, Floyd, A. G. and Jain, S., Injectable Emulsions and Suspensions, Chapter 7 in *Pharmaceutical Dosage Forms: Disperse Systems Vol. 2*, Edited by Lieberman, H. A., Rieger, M. M., and Banker, G. S., Marcel Dekker, New York (1996), the entirety of which is incorporated herein by reference and referred to herein as "the Floyd et al. Chapter").

Syringeability describes the ability of an injectable suspension to pass easily through a hypodermic needle on transfer from a vial prior to injection. It includes characteristics such as ease of withdrawal, clogging and foaming tendencies, and accuracy of dose measurements. As described in the Floyd et al. Chapter, increase in the viscosity, density, particle size, and concentration of solids in suspension hinders the syringeability of suspensions.

Injectability refers to the performance of the suspension during injection. Injectability includes factors such as pressure or force required for injection, evenness of flow, aspiration qualities, and freedom from clogging.

Clogging refers to the blockage of syringe needles while administering a suspension. It may occur because of a single large particle, or an aggregate that blocks the lumen of the needle due to a bridging effect of the particles. Clogging at or near the needle end may be caused by restrictions to flow from the suspension. This may involve a number of factors, such as the injection vehicle, wetting of particles, particle size and distribution, particle shape, viscosity, and flow characteristics of the suspension.

Resuspendability describes the ability of the suspension to uniformly disperse with minimal shaking after it has stood for some time. Resuspendability can be a problem for suspensions that undergo "caking" upon standing due to settling of the deflocculated particles. "Caking" refers to a process by which the particles undergo growth and fusion to form a nondispersible mass of material.

Viscosity describes the resistance that a liquid system offers to flow when it is subjected to an applied shear stress. A more viscous system requires greater force or stress to make it flow at the same rate as a less viscous system. A liquid system will exhibit either Newtonian or non-Newtonian flow based on a linear or a non-linear increase, respectively, in the rate of shear with the shearing stress. Structured vehicles used in suspensions exhibit non-Newtonian flow and are typically plastic, pseudoplastic, or shear-thinning with some thixotropy (exhibiting a decrease in viscosity with an increase in the rate of shear).

In design of injection vehicles, viscosity enhancers are added in order to retard settling of the particles in the vial and syringe. However, viscosity is typically kept low, in order to facilitate mixing, resuspension of the particles with the vehicle, and to make the suspension easier to inject (i.e., low force on the syringe plunger). For example, Lupron Depot from TAP Pharmaceuticals (mean particle size of approximately 8 µm) utilizes an injection vehicle with a viscosity of approximately 5.4 cp. The fluid phase of a suspension of Decapeptyl from DebioPharm (mean particle size of approximately 40 µm), when prepared as directed, has a viscosity of approximately 19.7 cp. Conventional parenteral suspensions are dilute, with limitations for viscosity because of syringeability and injectability constraints. See, for example, the Floyd, et al. Chapter noted above.

Injectable compositions containing microparticle preparations are particularly susceptible to injectability problems. Microparticle suspensions may contain 10-15% solids, as compared with 0.5-5% solids in other types of injectable suspensions. Microparticles, particularly controlled release microparticles containing an active agent or other type of substance to be released, range in size up to about 250 µm, as compared with a particle size of less than 5 µm recommended for IM or SC administration. The higher concentration of solids, as well as the larger solid particle size, make it more difficult to successfully inject microparticle suspensions. This is particularly true since it is also desired to inject the microparticle suspensions using as small a needle as possible to minimize patient discomfort.

Thus, there is a need in the art for an injectable composition with improved injectability. There is a particular need in the art for an injectable composition that solves the injectability problems associated with microparticle suspensions. The present invention, the description of which is fully set forth below, solves the need in the art for such injectable compositions.

SUMMARY OF THE INVENTION

The present invention relates to injectable compositions having improved injectability, and to methods for the preparation of such injectable compositions. In one aspect of the invention, a composition suitable for injection through a needle into a host is provided. The composition comprises microparticles having a polymeric binder, with a mass median diameter of at least about 10 µm. The composition also includes an aqueous injection vehicle (the injection vehicle not being the aqueous injection vehicle that consists of 3% by volume sodium carboxymethyl cellulose, 1% by volume polysorbate 20, 0.9% by volume sodium chloride, and a remaining percentage by volume of water). The microparticles are suspended in the injection vehicle at a concentration of greater than about 30 mg/ml to form a suspension, the fluid phase of the suspension having a viscosity of at least 20 cp at 20° C. In other embodiments, the fluid phase of the suspension has a viscosity at 20° C. of at least about 30 cp, 40 cp, 50 cp, and 60 cp. The composition may also comprise a viscosity enhancing agent, a density enhancing agent, a tonicity enhancing agent, and/or a wetting agent. The composition can be administered to a host by injection.

In another aspect of the present invention, a method of making a composition suitable for injection through a needle into a host is provided. The method comprises:
   (a) providing microparticles comprising a polymeric binder, said microparticles having a mass median diameter of at least about 10 µm;
   (b) providing an aqueous injection vehicle having a viscosity of at least 20 cp at 20° C., wherein said injection vehicle is not the aqueous vehicle consisting of 3% by volume sodium carboxymethyl cellulose, 1% by volume polysorbate 20, 0.9% by volume sodium chloride, and a remaining percentage by volume of water; and
   (c) suspending the microparticles in the aqueous injection vehicle at a concentration of greater than about 30 mg/ml to form a suspension.

In a further aspect of the present invention, another method for preparing a composition suitable for injection through a needle into a host is provided. In such a method, dry microparticles are mixed with an aqueous injection vehicle to form a first suspension. The first suspension is mixed with a viscosity enhancing agent to form a second suspension. The viscosity enhancing agent increases the viscosity of the fluid phase of the second suspension. The first suspension may be withdrawn into a first syringe, prior to mixing with the viscosity enhancing agent. The first suspension may be mixed with the viscosity enhancing agent by coupling the first syringe containing the first suspension to a second syringe that contains the viscosity enhancing agent. The first suspension and the viscosity enhancing agent are then repeatedly passed between the first and second syringes.

In yet a further aspect of the present invention, a method for administering a composition to a host is provided. The method comprises:
   (a) mixing dry microparticles with an aqueous injection vehicle to form a first suspension;
   (b) mixing the first suspension with a viscosity enhancing agent to form a second suspension, wherein the viscosity enhancing agent increases the viscosity of the fluid phase of the second suspension; and
   (c) injecting the second suspension into the host.

In still a further aspect of the present invention, another method for administering a composition to a host is provided. The method comprises:
   (a) mixing dry microparticles with an aqueous injection vehicle to form a suspension, wherein the aqueous injection vehicle has a viscosity at 20° C. of less than about 60 cp;
   (b) changing the viscosity of the fluid phase of the suspension;
   (c) withdrawing the suspension into a syringe; and
   (d) injecting the suspension from the syringe into the host.

In a further aspect of the invention, step (b) is carried out by changing the temperature of the fluid phase of the suspension. In another aspect, step (c) is performed prior to step (b). Step (b) may be carried out by adding a viscosity enhancing agent to the suspension in the syringe to thereby increase the viscosity of the fluid phase of the suspension.

In still a further aspect of the invention, a method for preparing a composition suitable for injection through a needle into a host is provided. The method comprises:
   (a) mixing dry microparticles with an aqueous injection vehicle that comprises a viscosity enhancing agent to form a suspension;
   (b) removing water from the suspension; and
   (c) reconstituting the suspension with a quantity of sterile water for injection to form an injectable suspension, wherein the quantity of sterile water for injection is sufficient to achieve a viscosity of a fluid phase of the injectable suspension that provides injectability of the composition through a needle ranging in diameter from 18-22 gauge.

Features and Advantages

A feature of the present invention is that the injectable compositions can be used to inject varying types of microparticles, and varying types of active agents or other substances, into a host.

A further feature of the present invention is that it allows microparticles to be wetted to achieve a homogeneous suspension, while improving injectability into a host and reducing in vivo injectability failures.

The present invention advantageously provides medically acceptable injectability rates for high concentration suspensions, and for suspensions having large particle size.

The present invention also advantageously provides an efficient method of improving in vivo injectability without introducing microbial contamination or compromising aseptic conditions.

DETAILED DESCRIPTION OF THE
PREFERRED EMBODIMENTS

Overview

The present invention relates to injectable compositions having improved injectability, and to methods for the preparation of such injectable compositions. The injectable compositions of the present invention overcome injectability problems, particularly injectability failures that occur upon injection into muscle or subcutaneous tissue. Such injectability failures will be referred to herein as "in vivo injectability failures." In vivo injectability failures often manifest themselves in the form of a plug at the tip of the needle, and occur immediately or shortly after injection has been initiated. In vivo injectability failures are typically not predicted by laboratory or other in vitro testing.

The inventors have unexpectedly discovered that injectability is improved, and in vivo injectability failures significantly and unexpectedly reduced, by increasing the viscosity of the fluid phase of an injectable suspension. This is in contrast to conventional teachings that an increase in the viscosity hinders injectability and syringeability.

Viscous vehicles, however, are not optimal for preparing homogeneous suspensions of microparticles because of the relative inability of viscous vehicles to penetrate and wet out a mass of dry particles. Suspensions prepared with viscous vehicles are prone to clump irreversibly. Consequently, such suspensions are not injectable via needles of medically acceptable size. A further disadvantage of viscous suspensions is the lack of ease of transferring such suspensions from the vial or container used to prepare the suspension to the syringe used for injection.

The present invention also solves the additional problems that arise from use of a viscous injection vehicle. In accordance with the present invention, microparticles are suspended in an injection vehicle having suitable wetting characteristics. The viscosity of the fluid phase of the injectable suspension is increased prior to injecting the suspension in order to improve injectability, and to reduce in vivo injectability failures.

To ensure clarity of the description that follows, the following definitions are provided. By "microparticles" or "microspheres" is meant particles that contain an active agent or other substance dispersed or dissolved within a polymer that serves as a matrix or binder of the particle. The polymer is preferably biodegradable and biocompatible. By "biodegradable" is meant a material that should degrade by bodily processes to products readily disposable by the body and should not accumulate in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weight" is meant parts by weight per hundred parts total weight of microparticle. For example, 10 wt. % active agent would mean 10 parts active agent by weight and 90 parts polymer by weight. Unless otherwise indicated to the contrary, percentages (%) reported herein are by volume. By "controlled release microparticle" or "sustained release microparticle" is meant a microparticle from which an active agent or other type of substance is released as a function of time. By "mass median diameter" is meant the diameter at which half of the distribution (volume percent) has a larger diameter and half has a smaller diameter.

METHOD AND EXAMPLES

The following examples are provided to explain the invention, and to describe the materials and methods used in carrying out the invention. The examples are not intended to limit the invention in any manner.

Example 1—In vitro Sieve Test Study

To evaluate in vivo injectability failures, an in vitro sieve test study was conducted to assess and predict in vivo injectability, and to determine the key factors affecting injectability. The following factors were investigated during the in vitro sieve test study: injection vehicle formulation; microparticle morphology; needle diameter; suspension concentration; and particle size as exhibited by sieve screen size used to screen the microparticles during the manufacturing process.

Three batches of risperidone microparticles were manufactured at a 125 gm scale using a process substantially the same as that disclosed in U.S. Pat. No. 5,792,477, the entirety of which is incorporated herein by reference (see, for example, Example 1 in U.S. Pat. No. 5,792,477). Three batches of risperidone microparticles were manufactured at a 1 Kg scale using the process described below in Example 7. All batches had similar particle sizes (ranging from a Mass Median Diameter of 91 µm to 121 µm) based on Hyac-Royco analysis of representative bulk material sieved through a 180 µm sieve screen. A 160 mg or 320 mg quantity of the microparticles (equivalent to a 50 or 100 mg dose of the risperidone active agent) was transferred, using a manual Perry powder filler with a 5/16 inch ID barrel, into a 5 cc glass vial, and capped with a Teflon lined septum.

Two injection vehicles were used in the in vitro sieve test study. The first injection vehicle ("Formula 1") was an aqueous vehicle consisting of 1.5% by volume carboxymethyl cellulose (CMC), 30% by volume sorbitol, and 0.2% by volume Tween 20 (polysorbate 20). The viscosity of the first injection vehicle was approximately 27 cp at 20° C. The second injection vehicle ("Formula 2") was an aqueous vehicle consisting of 0.75% by volume CMC, 15% by volume sorbitol, and 0.2% by volume Tween 20 (polysorbate 20). The viscosity of the second injection vehicle was approximately 7 cp at 20° C.

The microparticle suspension was prepared as follows. The injection vehicle was aspirated into a 5cc syringe through a needle. The vehicle was then injected into the glass vial containing the microparticles, and the needle was removed. The glass vial was then rolled between the palms until the microparticles were completely suspended, approximately one minute. The needle was reinserted into the vial so that the bevel of the needle was just through the septum with the opening facing toward the vial bottom. The vial was inverted and the suspension was withdrawn. The syringe was rotated 180° around its axis, and the remaining suspension was aspirated into the syringe.

Sieve screens with mesh opening sizes of 180, 212, 250, 300, 355, and 425 µm were used. The bevel of the syringe needle was placed on the mesh of the sieve screen so that the bevel was in full contact with the mesh. The needle was oriented so the opening of the needle was flush against the mesh of the screen. This prevented the mesh from entering the bevel, while maintaining the required restrictive area. The suspension was tried on the smallest sieve mesh first (highest screen resistance). If the suspension fouled the needle on this sieve mesh, the needle was unclogged by retracting the plunger of the syringe, depressing the plunger while the syringe was in the upward position, and passing an aliquot of suspension through the needle. The injection process was tried again using the next greater mesh size, and repeated until the suspension was successfully injected. All preparations were done in triplicate.

A three-factor Box-Behnken statistical designed experiment was constructed to evaluate the following independent variables: manufacturing bulk sieve size (125, 150, and 180 µm); needle ID (19 TW, 20 RW, and 22 RW gauge—ID of 19 TW (thin wall) equivalent to 18 RW (regular wall)); and suspension concentration (0.074, 0.096, and 0.138 w/w—corresponds to approximately 300 mg microparticle dose diluted with 4, 3, and 2 cc, respectively, of injection vehicle).

The following scoring system was used:

| Score | Result |
|---|---|
| 0 | Needle Block |
| 1 | Passes through a 425 µm screen |
| 2 | Passes through a 355 µm screen |
| 3 | Passes through a 300 µm screen |
| 4 | Passes through a 250 µm screen |
| 5 | Passes through a 212 µm screen |

Table 1 below shows the score obtained for screen resistance tests using this scoring system for the 1 Kg and the 125 gm batches for each of the injection vehicles tested.

TABLE 1

| Mfg Bulk Sieve Size | n | Mean Score Formula 2 ≈ 7 cp | Mean Score Formula 1 ≈ 27 cp |
|---|---|---|---|
| 1 Kg Batches | | | |
| <180 | 9 | 2.3 | 2.3 |
| <125 | 9 | 3.4 | 3.7 |
| 125 Gm Batches | | | |
| <180 | 6 | 1.5 | 2.0 |
| <150 | 6 | 3.0 | 2.8 |
| <125 | 6 | 3.0 | 2.5 |

As shown in Table 1, the screen resistance tests showed no significant difference between the two injection vehicles tested. Variations in suspension concentration and injection vehicle viscosity showed little to no effect. For the 1 Kg Batches, the mean scores were identical for the <180 manufacturing bulk sieve size, even though the viscosity of the Formula 1 injection vehicle was approximately 27 cp, and the viscosity of the Formula 2 injection vehicle was significantly less, approximately 7 cp. The scores for the other 1 Kg Batch and for the 125 Gm Batches varied modestly (0.2 to 0.5) between the two injection vehicles, thereby indicating that the injection vehicle viscosity had little effect. The tests conducted during the in vitro sieve test study show that in vitro injectability is strongly controlled by microparticle morphology and size. Needle gauge had a more modest effect. As will be discussed in more detail below, in vivo data supported the responses of microparticle morphology, size, and suspension concentration, but contradicted the effect of injection vehicle viscosity. Particularly, the in vivo studies showed a dramatic improvement in injectability with increased injection vehicle viscosity.

In vivo Injectability

Example 2—Pig Study

The injectability of risperidone microparticles was evaluated in Yorkshire weanling pigs. The study revealed that the IM injectability of risperidone microparticles is dependent upon injection vehicle viscosity and microparticle size. Reducing the injection vehicle viscosity led to a higher rate of injection failures due to needle clogging.

Risperidone microparticles were manufactured at the 125 gm scale in the same manner noted above for the in vitro sieve test study. The microparticles were sized to <125 μm and <150 μm using USA Standard Testing Sieves Nos. 120 and 100, respectively. The same two injection vehicles (Formula 1 and Formula 2) described above for the in vitro sieve test study were used in the pig study. 19 gauge TW×1.5 inch hypodermic needles (Becton-Dickinson Precisionglide® catalog number 305187) and 3 cc hypodermic syringes (Becton-Dickinson catalog number 309585) were used.

The injection experiments were conducted in male and female Yorkshire weanling pigs approximately 6 weeks in age (10-15 kg). The animals were anesthetized with low doses of Telazole and Xylazine and with halothane if needed. Injection sites were shaved and cleansed with betadine swabs prior to microparticle administration.

Injections to the hind-quarters were administered to the biceps femoris in the upper hind limb. Injection sites in the legs were to the superficial digital flexor muscles in the forelimb, and to the cranial tibial muscle in the hindlimb.

Microparticles and injection vehicles were equilibrated to ambient temperature for at least 30 minutes. Using a 3 ml syringe equipped with a 1.5 inch 19 gauge thin wall needle, the prescribed volume of injection vehicle was withdrawn into the syringe, and injected into the vial containing the microparticles. The microparticles were suspended in the injection vehicle by orienting the vial horizontally and rolling it between the palms of the operator's hands. This was done without removing the needle/syringe from the septum. The time required to fully suspend the microparticles was approximately one minute.

The suspended microparticles were then withdrawn into the same needle/syringe and injected. Following insertion of the needle and prior to injection of the suspension, the syringe plunger was withdrawn slightly to confirm that the needle was located in the extravascular space. The time interval between aspiration of the suspension and injection was usually less than one minute. Injection regions were evaluated to pinpoint the site of microparticle deposition and to assess the distribution of microparticles in the tissue.

Table 2 below shows the effect on injectability as a function of injection vehicle viscosity, injection site, and microparticle concentration. A vehicle viscosity of "high" refers to the injection vehicle of Formula 1 described above, having a viscosity of approximately 27 cp at 20° C. Similarly, a vehicle viscosity of "low" refers to the injection vehicle of Formula 2 described above, having a viscosity of approximately 7 cp at 20° C. The size of the microparticles for the results shown in Table 2 is 180 μm.

TABLE 2

| Vehicle Viscosity | Microparticle Dose | Volume | Site | Failure rate |
|---|---|---|---|---|
| High | 160 mg | 1 mL | Hind quarter | 0/10 |
| High | 160 mg | 1 mL | Leg | 1/8 |
| Low | 160 mg | 1 mL | Hind quarter | 4/7 |
| High | 320 mg | 1 mL | Hind quarter | 0/4 |

As can be seen from Table 2, increased failure rates were observed with the lower viscosity injection vehicle (4 failures with 7 injections), and when the injection site was in the leg (1 failure per 8 injections). The increased failure rate due to reduced viscosity was statistically significant at the 1% level (Fisher Exact Test).

Table 3 below summarizes injectability data for microparticles fractionated by size. Similar trends were observed when the system was stressed by decreasing the vehicle viscosity, with failure rates being higher with the <180 μm fraction. The <125 μm fraction and the <150 μm fraction were indistinguishable in terms of failure rate. The low viscosity data show statistically significant differences between <180 μm fraction and <150 μm fraction, and between <180 μm fraction and <125 μm fraction at 1% and 3% confidence levels, respectively (Fisher Exact Test).

TABLE 3

| Max. particle size (μm) | Vehicle Viscosity | Volume (mL) | Site | Failure rate | Avg. % delivered (failed injections)[1] |
|---|---|---|---|---|---|
| 180 | High | 2.0 | Leg | 0/5 | n/a |
| 150 | High | 2.0 | Leg | 0/5 | n/a |
| 125 | High | 2.0 | Leg | 0/5 | n/a |
| 180 | High | 1.0 | Leg | 2/4 | 0 |
| 150 | High | 1.0 | Leg | 0/4 | n/a |

TABLE 3-continued

| Max. particle size (μm) | Vehicle Viscosity | Volume (mL) | Site | Failure rate | Avg. % delivered (failed injections)[1] |
|---|---|---|---|---|---|
| 125 | High | 1.0 | Leg | 0/4 | n/a |
| 180 | Low | 2.0 | Hind quarter | 8/10 | 33 |
| 150 | Low | 2.0 | Hind quarter | 2/10 | 18 |
| 125 | Low | 2.0 | Hind quarter | 3/10 | 80 |

[1]Average fraction of dose delivered prior to needle clog (failed injections only)

The in vivo pig study demonstrates a lower injectability failure rate with a higher viscosity injection vehicle, over a range of particle sizes. The in vitro sieve test study did not predict the viscosity dependence observed in the pig study.

Example 3—Sheep Study

A two-part sheep study was conducted to investigate in vivo injectability as a function of injection vehicle composition and viscosity, and suspension concentration. In Part I, risperidone microparticles were prepared at the 1 Kg scale using the process described below in Example 7. A batch of placebo microparticles was prepared using the process shown and described in U.S. Pat. No. 5,922,253, the entirety of which is incorporated herein by reference. The two types of microparticles were studied at two suspension concentrations of 150 and 300 mg/ml. Animal injectability tests were conducted using 3 cc syringes and 22 gauge TW×1.5 inch needles (Becton-Dickinson).

Five injection vehicles were used in Part 1. The five injection vehicles were made using one or more of the three injection vehicle formulations shown below:

| Vehicle A | 0.9% Saline; 0.1% Tween 20 |
| Vehicle B | 1.5% CMC; 30% Sorbitol; 0.2% Tween 20 |
| Vehicle C | 3% CMC; 0.1% Tween 20; 0.9% Saline |

Animal studies were conducted using domestic sheep weighing approximately 100-150 pounds. The animals were anesthetized with Telazole/Xylazine/Atropine intramuscularly and further supplemented with isofluorane gas (approximately 1-2%) during the injection procedure. Prior to injection, the animal's dorsal, gluteal, and upper leg regions were shaved and cleaned with alcohol. Injection sites were visualized prior to and during dosing using ultrasound (EI Medical).

The microparticles and injection vehicles were equilibrated to ambient temperature prior to dose suspension. Using a 3 cc syringe and 22 gauge thin-walled needle, the vehicle was aspirated and injected into the microparticle vial. The risperidone microparticles were suspended in 1 ml of vehicle at approximate concentrations of 150 or 300 mg/ml. Placebo microparticles were suspended in 2 or 1 ml of vehicle at approximate concentrations of 150 or 300 mg/ml. The vial was then agitated by hand for approximately 1 minute until the microparticles were suspended. The suspension was then aspirated back into the syringe using the same needle. Care was taken to recover the maximum amount of suspension from the vial. Preparation of dose suspensions was conducted randomly by three individuals.

All doses were injected by a single individual into the animal almost immediately after preparation. The rate of injection was maintained constant at approximately 5-10 seconds.

The results from Part I are shown in Table 4 below. Viscosities were determined by Brookfield Model LVT viscometer fitted with a UL adapter. Densities were measured for Vehicles A, B, and C. Densities for the combination vehicles made up of Vehicles A, B, and C were determined by interpolation based upon the ratio of Vehicles A, B, and C in the combination vehicle.

TABLE 4

| Vehicle | Viscosity (cp) | Density (mg/ml) | Conc (mg/ml)[2] | Failures |
|---|---|---|---|---|
| Vehicle A | 1.0 | 1.01 | 150 | 8/10 |
| Vehicle B | 24.0 | 1.11 | 150 | 1/10 |
|  | 24.0 | 1.11 | 300 | 0/10 |
| Vehicle C | 56.0 | 1.04 | 150 | 0/10 |
|  | 56.0 | 1.04 | 150 | 1/10[1] |
|  | 56.0 | 1.04 | 300 | 0/10 |
| 3 Parts Vehicle B:1 Part Vehicle A | 11.1 | 1.08 | 300 | 0/5 |
| 1 Part Vehicle B:3 Parts Vehicle A | 2.3 | 1.03 | 300 | 7/10 |

[1]Placebo Microparticles. All other results are risperidone microparticles.
[2]mg microparticles/ml diluent In order to isolate the effect of injection vehicle viscosity on injectability, additional sheep injectability tests (Part II) were conducted. The injectability results are shown below in Table 5. Viscosities were determined by Brookfield Model LVT viscometer fitted with a UL adapter. In Part II, the suspension concentration was fixed at 300 mg/ml. The tests in Part II were carried out using risperidone microparticles prepared in the same manner as in Part I, using the same injection protocol. The injection vehicles included Vehicle C and Vehicle A as described above, as well as injection vehicles prepared by diluting Vehicle C with Vehicle A. For example, the injection vehicle formulation having a viscosity of 22.9 cp is formulated by combining Vehicle C and Vehicle A in a 1:1 ratio, thereby forming Diluent 1.

TABLE 5

| Vehicle | Viscosity (cp) | Density (mg/ml) | Conc (mg/ml) | Failures |
|---|---|---|---|---|
| Vehicle C | 63.8 | 1.04 | 300 | 2/10 |
| 1:1 Vehicle C:Diluent 1 | 37.6* | 1.03 | 300 | 2/10 |
| 1:1 Vehicle C:Vehicle A (Diluent 1) | 22.9 | 1.03 | 300 | 1/10 |
| 1:1 Diluent 1:Vehicle A (Diluent 2) | 11.3 | 1.02 | 300 | 5/10 |
| 1:1 Diluent 2:Vehicle A | 1.4 | 1.01 | 300 | 7/10 |
| Vehicle A | 1 | 1.01 | 300 | 10/10 |

*estimate, insufficient sample

The data for Parts I and II shown in Tables 4 and 5 clearly show that the injection vehicle viscosity has an effect on injectability. Viscosities of at least about 20 cp are necessary for successful and medically acceptable injectability rates. At viscosities of less than or equal to about 11 cp, in vivo injectability failures increase significantly.

The effect of a density enhancing agent can be seen by comparing the injectability failures using the vehicle in Table 4 having a viscosity of 11.1 cp with the vehicle in Table 5 having a viscosity of 11.3 cp. The viscosity of these two vehicles is nearly the same. However, the Table 4 vehicle had 0/5 failures while the Table 5 vehicle had 5/10 failures. The Table 4 vehicle has a higher density (1.08 mg/ml) compared to the Table 5 vehicle (1.02 mg/ml). The Table 4 vehicle includes a density enhancing agent, sorbitol, while the Table 5 vehicle contains no sorbitol or other density enhancing agent.

Example 4—Ex Vivo Injectability Tests

Injectability tests were conducted with several injection vehicles prepared at viscosities exceeding ~50 cp. Injection vehicles having viscosities in excess of 50 cp were mixed, using a syringe-syringe mixing method described in more detail in Example 5 below, in which the viscosity enhancing agent was introduced after suspending the microparticles in the 50 cp vehicle.

Subcutaneous injections of blank (placebo) PLGA (poly (d,l-lactic-co-glycolic acid)) microparticles, having an approximate mass median diameter of 50 μm, were made into previously harvested pig skin using four injection vehicles having viscosities at ~25° C. of approximately 53.1 to >1000 cp at the time of formulation. The vehicles were subsequently autoclaved before use, and the final viscosity (viscosity of the fluid phase of the injectable suspension) varied between approximately 5-60% from the nominal starting viscosity value. The most viscous injection vehicle was approximately 13 times the viscosity of the 50 cp formulation. In this ex vivo model, increasing the viscosity of the fluid phase of the injectable suspension decreased injection failure rate, even when microparticle concentration was raised from 175 to 250 mg/ml, at a needle size of 22 G. Maximal improvement in injectability, within this range of concentration and needle size, was achieved with injection vehicles having a viscosity of approximately 250 cp.

In another study, four injection vehicles having measured viscosities of 53 to 251 cp were evaluated for subcutaneous injectability in anesthetized pigs. Microparticle concentrations were 150 and 190 mg/ml. Injection failure was directly related to microparticle concentration, and inversely related to viscosity level. At 53 cp, approximately 50% of injections failed, while at higher viscosities, failures diminished. At the highest viscosity (251 cp), zero failures were recorded at both microparticle concentrations.

Example 5—Methods for Preparing Injectable Compositions

Methods for preparing injectable compositions in accordance with the present invention will now be described. In accordance with the present invention, microparticles are first mixed with an injection vehicle having suitable viscosity and wetting characteristics to achieve a homogeneous mono-particulate suspension. The viscosity of the fluid phase of the suspension is then changed, preferably increased, to achieve a viscosity that inhibits suspension separation and clogging under conditions of normal clinical use. In accordance with one method of the present invention, dry microparticles are mixed with an aqueous injection vehicle to form a first suspension. The first suspension is mixed with a viscosity enhancing agent to form a second suspension. The viscosity enhancing agent increases the viscosity of the fluid phase of the second suspension. The second suspension is then injected into a host.

One embodiment for carrying out such a method will now be described. Vialed dry microparticles are mixed with an aqueous injection vehicle having a viscosity less than about 60 cp at 20° C., preferably about 20-50 centipoise. The concentration of microparticles in the mixture is greater than about 30 mg/ml, preferably about 100-400 mg microparticles/ml. The mixture is agitated until a homogeneous suspension is formed. The homogeneous suspension is withdrawn into a first hypodermic syringe. The first syringe is connected to a second syringe containing a viscosity enhancing agent. A viscosity enhancing agent suitable for use with the present invention is sodium carboxymethyl cellulose (CMC), preferably having a viscosity of from about 1000 to about 2000 cp at 20° C. It should be understood that the present invention is not limited to the use of CMC as the viscosity enhancing agent, and other suitable viscosity enhancing agents may be used. The added volume of the viscosity enhancing agent is approximately 10-25% of the volume of the microparticle suspension.

The microparticle suspension and the viscosity enhancing agent are mixed to form the injectable composition by repeatedly passing the microparticle suspension and the viscosity enhancing agent between the first and second syringes. Such a syringe-syringe mixing method was used in the injectability tests described in Example 4 above. After mixing with the viscosity enhancing agent, the viscosity of the fluid phase of the microparticle suspension is from about 200 cp to about 600 cp at 20° C. A hypodermic needle is attached to the syringe containing the injectable composition, and the injectable composition is injected into a host in a manner well known to one of skill in the art.

An alternate embodiment for carrying out the method of the present invention will now be described. Dry microparticles are mixed with an aqueous injection vehicle having a viscosity of less than about 60 cp at 20° C. to form a suspension. The viscosity of the fluid phase of the suspension is changed in a manner that will be described in more detail below. The suspension that constitutes the injectable composition is withdrawn into a syringe, and the injectable composition is injected from the syringe into the host. Preferably, the viscosity of the fluid phase of the suspension is changed after the suspension has been withdrawn into the syringe.

In one aspect of this alternate embodiment, the viscosity is changed by changing the temperature of the fluid phase of the injectable suspension. The methods and techniques for changing the viscosity of a liquid by changing the temperature of the liquid are readily apparent to one skilled in the art. The temperature of the fluid phase of the suspension is changed until the desired viscosity of the fluid phase has been reached. The suspension now has the desired fluid phase viscosity for injection into a host, and constitutes the injectable composition. At this point, the suspension is withdrawn into the syringe and injected into the host. Alternatively, the suspension can be withdrawn into the syringe prior to changing the temperature of the fluid phase of the suspension to achieve the desired fluid phase viscosity. For example, an injection vehicle that comprises a polymer solution can be used as the viscosity of polymer solutions is temperature-dependent. A polymer solution can be used to suspend the microparticles under low-viscosity conditions suitable for wetting and suspension formation. Once the microparticles are suspended, the suspension is drawn up into a syringe. The temperature is then changed to induce higher viscosity in the injection vehicle constituting the fluid phase of the suspension, and the suspension having increased viscosity is injected into a host.

In another aspect of this alternate embodiment, the viscosity is changed by adding a viscosity enhancing agent to the suspension. The suspension is withdrawn into the syringe, and then the viscosity enhancing agent is added to the suspension in the syringe, thereby increasing the viscosity of the aqueous injection vehicle constituting the fluid phase of the suspension. The suspension now has the desired fluid phase viscosity for injection into a host, and constitutes the injectable composition. The suspension is then injected into the host. Preferably, the viscosity enhancing agent is added to the suspension immediately prior to injection into the host. Suitable viscosity enhancing agents include sodium carboxymethyl cellulose, polyvinylpyrrolidone (PVP), such as PLASDONE, available from GAF Chemicals Corp., Wayne, N.J., and hydroxypropylmethylcellulose (HPMC), such as Methocel, available from Dow Chemical Co., Midland, Mich. However, other viscosity enhancing agents may be used, as would be readily apparent to one of skill in the art.

In another embodiment of the invention, the injectable compositions of the present invention are prepared by providing microparticles that comprise a polymeric binder and that have a mass median diameter of at least about 10 μm. The mass median diameter of the microparticles is preferably less than about 250 μm, and more preferably, in the range of from about 20 μm to about 150 μm. Such microparticles can be made in the manner disclosed and described herein, or in any other manner known to one skilled in the art. An aqueous injection vehicle is provided. Such an aqueous injection vehicle can be made in the manner disclosed and described herein, or in any other manner known to one skilled in the art. The microparticles are suspended in the aqueous injection vehicle at a concentration of greater than about 30 mg/ml to form a suspension, the fluid phase of the suspension having a viscosity of at least 20 cp at 20° C.

In yet a further embodiment of the present invention, dry microparticles are mixed with an aqueous injection vehicle containing a viscosity enhancing agent to form a suspension. Suitable viscosity enhancing agents include sodium carboxymethyl cellulose, polyvinylpyrrolidone (PVP), such as PLASDONE, available from GAF Chemicals Corp., Wayne, N.J., and hydroxypropylmethylcellulose (HPMC), such as Methocel, available from Dow Chemical Co., Midland, Mich. However, other viscosity enhancing agents may be used, as would be readily apparent to one of skill in the art. The suspension is then dispensed into vials. The vials are lyophilized (or vacuum dried) to remove the water. Prior to injection, the vial contents are reconstituted with sterile water for injection in a quantity sufficient to achieve the desired viscosity for the fluid phase of the reconstituted injectable suspension. Preferably, the vial contents are reconstituted with a quantity of sterile water for injection sufficient to achieve a viscosity of a fluid phase of the injectable suspension that provides injectability of the composition through a needle ranging in diameter from 18-22 gauge.

Example 6—Injectable Compositions

The injectable compositions of the present invention will now be described. The injectable compositions of the present invention are suitable for injection through a needle into a host. In one embodiment, the injectable compositions comprise microparticles suspended in an aqueous injection vehicle. The microparticles preferably have a mass median diameter of at least about 10 μm to about 250 μm, preferably in the range of from about 20 μm to about 150 μm. However, it should be understood that the invention is not limited to microparticles in this size range, and that smaller or larger microparticles may also be used.

The microparticles preferably comprise a polymeric binder. Suitable polymeric binder materials include poly (glycolic acid), poly-d,l-lactic acid, poly-l-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, polyphosphazines, albumin, casein, and waxes. Poly (d,l-lactic-co-glycolic acid) is commercially available from Alkermes, Inc. (Blue Ash, Ohio). A suitable product commercially available from Alkermes, Inc. is a 50:50 poly(d,l-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,l-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,l-PLA (Resomer® RG 206), and from Birmingham Polymers (Birmingham, Ala.). These copolymers are available in a wide range of molecular weights and ratios of lactic acid to glycolic acid.

One type of microparticle suitable for use with the present invention is a sustained-release microparticle that is biodegradable. However, it should be understood by one skilled in the art that the present invention is not limited to biodegradable or other types of sustained-release microparticles. As would be apparent to one skilled in the art, the molecular weight of the polymeric binder material for biodegradable microparticles is of some importance. The molecular weight should be high enough to permit the formation of satisfactory polymer coatings, i.e., the polymer should be a good film former. Usually, a satisfactory molecular weight is in the range of 5,000 to 500,000 daltons, preferably about 150,000 daltons. However, since the properties of the film are also partially dependent on the particular polymeric binder material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric binder bioerodes. By an appropriate selection of polymeric materials a microparticle formulation can be made in which the resulting microparticles exhibit both diffusional release and biodegradation release properties. This is useful in according multiphasic release patterns.

The microparticles may include an active agent or other type of substance that is released from the microparticles into the host. Such active agents can include 1,2-benzazoles, more particularly, 3-piperidinyl-substituted 1,2-benzisoxazoles and 1,2-benzisothiazoles. The most preferred active agents of this kind are 3-[2-[4-(6-fluoro-1,2-benzisoxazol-3-yl)-1-piperidinyl ethyl]-6,7,8,9-tetrahydro-2-methyl-4H--pyrido[1,2-a]pyrimidin-4-one ("risperidone") and 3-[2-[4-(6-fluro-1,2-benzisoxazol-3-yl)-1-piperid ethyl]-6,7,8,9-tetrahydro-9-hydroxy-2-methyl-4H--pyrido[1,2-a] pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents include non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-Parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodienone, meperidine, morphine and the like; non-narcotics such as salicylates, aspirin, acetaminophen, d-propoxyphene and the like; opioid receptor antagonists, such as naltrexone and naloxone; antibiotics such as gentamycin, tetracycline and penicillins; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs.

Still other suitable active agents include estrogens, antibacterials; antifungals; antivirals; anticoagulants; anticonvulsants; antidepressants; antihistamines; and immunological agents.

Other examples of suitable biologically active agents include peptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, carboplatin, methotrexate and adriamycin; antipyretic and analgesic agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and heparin; hemostatic agents such as thrombin, menadione sodium bisulfite and acetomenaphthone; antituberculous agents such as isoniazide and ethanbutol; hormones such as prednisolone sodium phosphate and methimazole.

The microparticles can be mixed by size or by type. However, it should be understood- that the present invention is not limited to the use of biodegradable or other types of microparticles that contain an active agent. In one embodiment, the microparticles are mixed in a manner that provides for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

The microparticles are preferably suspended in the injection vehicle at a concentration of greater than about 30 mg/ml. In one embodiment, the microparticles are suspended at a concentration of from about 150 mg/ml to about 300 mg/ml. In another embodiment, the microparticles are suspended at a concentration of from about 100 mg/ml to about 400 mg/ml. However, it should be understood that the invention is not limited to a particular concentration.

The aqueous injection vehicle preferably has a viscosity of at least 20 cp at 20° C. In one embodiment, the injection vehicle has a viscosity greater than 50 cp and less than 60 cp at 20° C. The viscosity of the injection vehicle preferably provides injectability of the composition through a needle ranging in diameter from 18-22 gauge. As known to one skilled in the art, an 18 gauge regular wall (RW) needle has a nominal inner diameter (ID) of 0.033 in., and a 22 gauge regular wall needle has a nominal inner diameter of 0.016 in.

The injection vehicle may comprise a viscosity enhancing agent. A preferred viscosity enhancing agent is sodium carboxymethyl cellulose, although other suitable viscosity enhancing agents may also be used. The injection vehicle may also comprise a density enhancing agent that increases the density of the injection vehicle. A preferred density enhancing agent is sorbitol, although other suitable density enhancing agents may also be used. The injection vehicle may also comprise a tonicity adjusting agent to adjust the tonicity to preclude toxicity problems and improve biocompatibility. A preferred tonicity adjusting agent is sodium chloride, although other suitable tonicity adjusting agents may also be used.

The injection vehicle may also comprise a wetting agent to ensure complete wetting of the microparticles by the injection vehicle. Preferred wetting agents include polysorbate 20 (Tween 20), polysorbate 40 (Tween 40), and polysorbate 80 (Tween 80).

One preferred injection vehicle is an aqueous injection vehicle that comprises 1.5% sodium carboxymethyl cellulose, 30% sorbitol, and 0.2% polysorbate 20. Another preferred injection vehicle is an aqueous injection vehicle that comprises 3% sodium carboxymethyl cellulose, 0.9% saline, and 0. 1% polysorbate 20.

Example 7—1 Kg Process

A process for preparing microparticles containing risperidone as the active agent will now be described. The following 1 Kg process (400 grams of active agent and 600 grams of polymer) is for a theoretical drug loading of the microparticles of 40%. The actual drug loading that is achieved by the process described below ranges from about 35% to about 39%.

A drug solution is prepared by dissolving 400 grams of risperidone (Janssen Pharmaceutica, Beerse, Belgium) in 1267 grams of benzyl alcohol to form a 24 wt. % drug solution. A polymer solution is formed by dissolving 600 grams of MEDISORB® 7525 DL polymer (Alkermes, Inc., Blue Ash, Ohio) in 3000 grams of ethyl acetate to form a 16.7 wt. % polymer solution. The drug solution and the polymer solution are combined to form a first, discontinuous phase.

The second, continuous phase is prepared by preparing a 30 liter solution of 1% PVA, the PVA acting as an emulsifier. To this is added 2086 grams of ethyl acetate to form a 6.5 wt. % solution of ethyl acetate.

The two phases are combined using a static mixer, such as a ½" Kenics static mixer available from Chemineer, Inc., North Andover, Mass. A total flow rate of 3 L/min generally provides microparticle size distributions with a mass median diameter (MMD) in the range of about 80-90μ. The ratio of continuous phase to discontinuous phase is 5:1 (v/v). The length of the static mixer can vary from about 9 inches to about 88 inches. Lengths greater than about 48 inches results in the greatest percent yield in a microparticle size range of 25-150μ.

The quench liquid is 2.5% solution of ethyl acetate and water-for-injection (WFI) at 5-10° C. The volume of the quench liquid is 0.25 L per gram of batch size. The quench step is carried out for a time period greater than about 4 hours, with stirring of the microparticles in the quench tank.

After completion of the quench step, the microparticles are transferred to a collecting, de-watering, and drying device. The microparticles are rinsed using a chilled (approximately 5° C.) 17 liter 25% ethanol solution. The microparticles are dried, and then re-slurried in a re-slurry tank using a 25% ethanol solution (extraction medium) maintained at a temperature lower than the $T_g$ (glass transition temperature) of the microparticles. The microparticles are then transferred back to the quench tank for washing for a time period of at least 6 hours with another extraction medium (25% ethanol solution) that is maintained at a temperature higher than the $T_g$ of the microparticles. The $T_g$ of the microparticles is about 18° C. (about room temperature), and the temperature of the extraction medium in the quench tank is greater than about 18° C., preferably 25±1° C.

The microparticles are transferred back to the collecting, de-watering, and drying device for de-watering and final drying. Drying continues for a time period greater than about 16 hours.

CONCLUSION

While various embodiments of the present invention have been described above, it should be understood that they have been presented by way of example only, and not limitation. The present invention is not limited to controlled release microparticle injectable -suspensions, nor is it limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents.

What is claimed is:

1. A method for preparing a composition suitable for injection through a needle into a host, comprising:
    (a) mixing dry microparticles with an injection vehicle to form a first suspension, wherein the microparticles comprise a polymeric binder and wherein the microparticles are suspended in the injection vehicle at a concentration of from about 175 mg/ml to about 400 mg/ml; and
    (b) mixing the first suspension with a viscosity enhancing agent to form a second suspension, wherein the viscosity enhancing agent increases viscosity of a fluid phase of the second suspension to be in the range of from about 20 cp to about 600 cp at 20° C., wherein the viscosity of the fluid phase of the second suspension provides injectability of the composition into the host through a needle ranging in diameter from 18-22 gauge.

2. The method of claim 1, wherein the viscosity of the fluid phase of the second suspension after step (b) is from about 200 cp to about 600 cp at 20° C.

3. The method of claim 1, wherein the concentration of microparticles in the first suspension is greater than about 300 mg/ml and less than about 400 mg/ml.

4. The method of claim 1, wherein a viscosity of the viscosity enhancing agent is from about 1000 to about 2000 cp at 20° C.

5. The method of claim 1, wherein the viscosity enhancing agent comprises sodium carboxymethyl cellulose.

6. The method of claim 1, wherein a volume of the viscosity enhancing agent mixed with the first suspension is approximately 10-25% of the volume of the first suspension.

7. The method of claim 1, further comprising before step (b):
    (c) withdrawing the first suspension into a first syringe.

8. The method of claim 7, wherein step (b) comprises:
    (i) providing a second syringe containing the viscosity enhancing agent;
    (ii) coupling the first syringe to the second syringe so that fluid can pass between the first and second syringes; and
    (iii) repeatedly passing the first suspension and the viscosity enhancing agent between the first and second syringes.

9. A method for administering a composition to a host, comprising:
    (a) mixing dry microparticles with an injection vehicle to form a first suspension, wherein the microparticles comprise a polymeric binder and wherein the microparticles are suspended in the injection vehicle at a concentration of from about 175 mg/ml to about 400 mg/ml;
    (b) mixing the first suspension with a viscosity enhancing agent to form a second suspension, wherein the viscosity enhancing agent increases viscosity of a fluid phase of the second suspension to be in the range of from about 20 cp to about 600 cp at 20° C. wherein the viscosity of the fluid phase of the second suspension provides injectability of the composition into the host; and
    (c) injecting the second suspension into the host through a needle ranging in diameter from 18-22 gauge.

10. A method for administering a composition to a host, comprising:
    (a) mixing dry microparticles with an injection vehicle to form a suspension, wherein the injection vehicle has a viscosity at 20° C. of less than about 60 cp, wherein the microparticles comprise a polymeric binder and wherein the microparticles are suspended in the injection vehicle at a concentration of from about 175 mg/ml to about 400 mg/ml;
    (b) changing the viscosity of a fluid phase of the suspension to be in the range of from about 20 cp to about 600 cp at 20° C. wherein the viscosity of the fluid phase of the second suspension provides injectability of the composition into the host;

(c) withdrawing the suspension into a syringe; and
(d) injecting the suspension from the syringe into the host through a needle ranging in diameter from 18-22 gauge.

11. The method of claim 10, wherein step (b) comprises: changing the temperature of the fluid phase of the suspension.

12. The method of claim 10, wherein step (c) is performed prior to step (b), and step (b) comprises:
adding a viscosity enhancing agent to the suspension in the syringe to thereby increase the viscosity of the fluid phase of the suspension.

13. The method of claim 12, wherein the viscosity enhancing agent comprises sodium carboxymethyl cellulose.

14. The method of claim 9, wherein the microparticles comprise an active agent.

15. A method of making a composition suitable for injection through a needle into a host, comprising:
(a) providing microparticles comprising a polymeric binder;
(b) providing an injection vehicle having a viscosity of at least 20 cp at 20° C.; and
(c) suspending the microparticles in the injection vehicle to form a suspension, wherein the microparticles are suspended in the injection vehicle at a concentration of from about 175 mg/ml to about 400 mg/ml, wherein the viscosity of a fluid phase of the suspension is in the range of from about 20 cp to about 600 cp at 20° C., wherein the viscosity of the fluid phase of the suspension provides injectability of the composition into the host through a needle ranging in diameter from 18-22 gauge.

16. The method of claim 10, wherein step (c) is performed prior to step (b).

17. A method for preparing a composition suitable for injection through a needle into a host, comprising:
(a) mixing dry microparticles with an injection vehicle to form a first suspension, wherein the microparticles comprise a polymeric binder and wherein the microparticles are suspended in the injection vehicle at a concentration of from about 175 mg/ml to about 400 mg/ml; and
(b) mixing the first suspension with a viscosity enhancing agent to form a second suspension, wherein the viscosity enhancing agent increases viscosity of a fluid phase of the second suspension to be in the range of from about 20 cp to about 600 cp at 20° C., wherein the viscosity of the fluid phase of the second suspension provides injectability of the composition into the host through a needle of medically acceptable size.

18. The method of claim 17, wherein an internal diameter of the needle ranges from about 700 to about 400 microns.

19. A method of making a composition suitable for injection through a needle into a host, comprising:
suspending microparticles comprising a polymeric binder in an injection vehicle having a viscosity of at least 20 cp at 20° C. to form a suspension, wherein the microparticles are suspended in the injection vehicle at a concentration of from about 175 mg/ml to about 400 mg/ml, wherein the viscosity of a fluid phase of the suspension is in the range of from about 20 cp to about 600 cp at 20° C., wherein the viscosity of the fluid phase of the suspension provides injectability of the composition into the host through a needle of medically acceptable size.

20. The method of claim 19, wherein an internal diameter of the needle ranges from about 700 to about 400 microns.

* * * * *